United States Patent
Wernet et al.

(10) Patent No.: US 6,879,708 B2
(45) Date of Patent: Apr. 12, 2005

(54) PLANAR PARTICLE/DROPLET SIZE MEASUREMENT TECHNIQUE USING DIGITAL PARTICLE IMAGE VELOCIMETRY IMAGE DATA

(75) Inventors: Mark P. Wernet, Sheffield Village, OH (US); Amy F. Mielke, Cleveland, OH (US); Jaikrishnan R. Kadambi, Richmond Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 647 days.

(21) Appl. No.: 09/865,137

(22) Filed: May 24, 2001

(65) Prior Publication Data

US 2002/0176606 A1 Nov. 28, 2002

(51) Int. Cl.$^7$ ................................................. G06K 9/00
(52) U.S. Cl. ............................ 382/107; 73/488; 356/28
(58) Field of Search ................................. 382/103, 104, 382/107; 73/488; 348/454, 155; 356/27, 28, 28.5

(56) References Cited

U.S. PATENT DOCUMENTS

| | | | | |
|---|---|---|---|---|
| 4,885,473 A | * | 12/1989 | Shofner et al. | .............. 250/574 |
| 5,231,463 A | * | 7/1993 | Shambaugh | ................ 356/336 |
| 5,701,172 A | | 12/1997 | Azzazy | |
| 6,289,126 B1 | * | 9/2001 | Ishisaka | ..................... 382/205 |
| 6,399,390 B1 | * | 6/2002 | Kantzas et al. | ............... 436/57 |
| 2001/0040214 A1 | * | 11/2001 | Friedman et al. | ........... 250/287 |
| 2003/0066358 A1 | * | 4/2003 | King | ....................... 73/861.11 |

OTHER PUBLICATIONS

Mercadier et al. ("Reflectography applied to Optical Particle Sizing: Theoretical and Experimental approaches", Proc, 2nd Int. Cong. OPT. Part. Siz, Tuscon, Arizona, pp. 258–268, 1990).*

"An LDA Technique for In Situ Simultaneous Velocity and Size Measurement of Large Spherical Particles in a Two–Phase Suspension Flow" by S. L. Lee and J. Srinivasan, *J. Multiphase Flow*, vol. 8, No. 1, pp. 47–57, 1982.

"Droplet sizing interferometry: a compairson of the visibility and phase/Doppler techniques" by T. A. Jackson and G. S. Samuelsen, *Applied Optics*, vol. 26, No. 11, pp. 2137–2143, Jun. 1987.

"Phase/Doppler spray analyzer for simultaneous measurements of drop size and velocity distributions" by W. D. Bachalo and M. J. Houser, *Optical Engineering*, vol. 23, No. 5, pp. 583–590, Sep./Oct. 1984.

"Droplet Sizing Using the Shifrin Inversion" by R. Albert and P. V. Farrell, *Journal of Fluids Engineering*, vol. 116, pp. 357–362, Jun. 1994.

"Full–field diffraction particle sizing" by M. A. Coil and P. V. Farrell, *Applied Optics*, vol. 34, No. 33, pp. 7771–7786, Nov. 20, 1995.

"Particle Sizing Using a Two–Dimensional Image" by P. V. Farrell, *SAE Paper 910725*, pp. 1273–1283, 1991.

(Continued)

Primary Examiner—Samir Ahmed
Assistant Examiner—Anand Bhatnagar
(74) Attorney, Agent, or Firm—Benesch, Friedlander, Coplan & Aronoff LLP

(57) ABSTRACT

A method for determining a mass flux of an entrained phase in a planar two-phase flow records images of particles in the two-phase flow. Respective sizes of the particles (the entrained phase) are determined as a function of a separation between spots identified on the particle images. Respective velocities of the particles are determined. The mass flux of the entrained phase is determined as a function of the size and velocity of the particles.

16 Claims, 4 Drawing Sheets

OTHER PUBLICATIONS

"Development of Particle Image Velocimetry for Multiphase Flow Diagnostics" by V. Palero and P. Arroyo, *Journal of Visualization*, vol. 1, No. 2, pp. 171–181, 1998.

"Particle displacement tracking technique and Cramer–Rao lower bound error in centroid estimates from CCD imagery" by Marl. P. Wernet and A. Pline, *Thirteenth Symposium on Turbulence* sponsored by University of Missouri–Rolla, Sep. 21–23, 1992.

"Fundamentals of digital particle image velocimetry" by J. Westerweel, *Meas. Sci. Technol.*, V. 8, pp. 1379–1392, 1997.

"Glare spot image calculations for a spherical particle illuminated by a tightly focused beam" by S. A. Schaub, D. R. Alexander, and J. P. Barton, *J. Opt. Soc. Am.*, vol. 9, No. 2, pp. 316–330, Feb. 1992.

"Glare points" by H. C. van de Hulst and R. T. Wang, *Applied Optics*, vol. 30, No. 33, pp. 4755–4763, Nov. 20, 1991.

"Non–Debye enhancements in the Mie scattering of light from a single water droplet" by James A. Lock and Judith R. Woodruff, *Applied Optics*, vol. 28, No. 3, pp. 523–529, Feb. 1, 1989.

"Observation of optical resonances of dielectric spheres by light scattering" by A. Ashkin and J. M. Dziedzic, *Applied Optics*, vol. 20, No. 10, pp. 1803–1814, May 15, 1981.

"Planar Measurements of Droplet Velocities and Size Within a Simplex Atomizer" by D. C. Herpfer and S. Jeng, *AIAA Journal*, vol. 35, No. 1, pp. 127–132, Jan. 1997.

"Multi–Intensity–Layer PIV application to a practical burner" by N. Yamada, Y. Ikeda and T. Nakajima, *10th International Symposium on the Application of Laser Techniques to Fluid Mechanics*, paper 30.4, Lisbon, Portugal, 2000.

"Particle Size Determination by Fourier Transform of Scattered Light" by R. F. Crouse and P. Latimer, *Proc. 2nd Int. Cong. Opt. Part. Siz*, Tucson, Arizona, 1990.

"Reflectography Applied to Optical Particle Sizing: Theoretical and Experimental Approaches", *Proc. 2nd Int. Cong. Opt. Part. Siz*, Tuscon, Arizona, 1990.

"Laser Sheet Dropsizing of dense sprays" by P. Le Gal, N. Farrugia, and D. A. Greenhalgh, *Optics & Laser Technology*, V. 31, pp. 75–83, 1999.

"Theory of the observations made of high–order rainbows from a single water droplet" by J. A. Lock, *Applied Optics*, V. 26, No. 24, pp. 5291–5298, Dec. 15, 1987.

* cited by examiner

PLANAR PARTICLE/DROPLET SIZE MEASUREMENT TECHNIQUE USING DIGITAL PARTICLE IMAGE VELOCIMETRY IMAGE DATA

This invention was made with government support under Grant No. NGT 3-52352 NASA Glenn Research Center and Grant No. NAG3-2110 NASA Glenn Research Center.

BACKGROUND OF THE INVENTION

The present invention relates to particle sizing. It finds particular application in conjunction with two-phase flows and will be described with particular reference thereto. It will be appreciated, however, that the invention is also amenable to other like applications.

Two-phase flows are used in many fuel combustion processes such as those found in gas turbine combustors, coal furnaces for power generation, and diesel engines. The efficiency of two-phase flows directly impacts the efficiency of the associated combustion process. For many industrial and fossil fuel energy processes, both the droplet/particle size and spatial distribution are of interest. The useful diagnostic tools should be able to make in situ measurements without disturbing the flow field so that the measurements can be meaningful for understanding these flows. This suggests the need for a novel non-intrusive optical technique that can provide instantaneous measurements of particle size and velocity at multiple spatial points in planar (2-D) fields so that estimates of the mass flow are obtained.

Digital Particle Image Velocimetry (DPIV) is a technique for obtaining planar measurements of particulate seeded flow fields. Light from a pulsed laser is formed into a thin sheet to illuminate a planar cross section of a flow. A CCD camera is used to record the light scattered by the particles at the two (2) instants that the light sheet is pulsed. The fluid velocity is determined by analyzing the recorded particle image data. Typically, cross-correlation data analysis is used to reduce the recorded image data to determine the fluid velocities. In most instances, the flow field is artificially seeded with tracer particles in order to measure the flow velocity. In two-phase flows, the second phase material provides the scattering sites for estimation of the flow velocity, or at least the velocity of the second phase. The objective of this work is to determine the feasibility of estimating particle size from Particle Image Velocimetry (PIV) image data. Particle size information can most likely be extracted provided the imaged particle size exceeds the optical system blur circle. The other major factors affecting the accuracy to which particle size information can be extracted are the optical system f/number, image system pixel resolution and dynamic range, the optical properties of the particles, and the characteristics of the scattered light from the particles.

Many different optical techniques for making in situ measurements of particle/droplet sizes are known.

An in-line holography system has been used to record holographic images of the light scattered from particles in a fluid. The hologram has been shown to be that of a screen with a circular aperture representing the particle image. Holograms have been reconstructed by passing a laser beam through the hologram and recording the reconstructed image at an on-axis observation plane. The reconstructed image contains the Fraunhofer pattern of the imaged particles. The size and shape of the particle is then determined by direct observation of the reconstructed image. Holography has been easily extended to velocity measurement by using double exposure holograms and analyzing the double aperture type of fringe structure in the reconstructed image to calculate the particle separation.

Laser interferometry has been used to characterize particles using the spatial frequency of the far-field fringe pattern in the forward-scatter region. Ovryn 4 uses partially coherent light and forward scattering to obtain Poisson Spot images of particles suspended in a solution to determine their 3-D velocities. Although not a sizing technique, this work illustrates the information content in the diffraction rings surrounding coherently illuminated particles and such rings are used to determine additional properties about the particle. The difficulty with these holographic and interferometric techniques lies in the requirement of a high spatial resolution detection media, typically photographic film.

Phase Doppler Particle Analysis (PDPA) is an existing technique that is able to make point wise velocity and size measurements simultaneously. Droplet sizes are obtained using PDPA, which relates the droplet size to the phase shift of light refracted through the drop and scattered to different positions on the receiving lens. The technique known as Laser Doppler Anemometry (LDA), which is a technique for obtaining point wise velocity measurements, has been modified for applications to particle sizing as well. The particular modifications relate the particle diameter to the LDA signal visibility. Other variations of the technique relate either the scattered intensity or the phase shift of the scattered light to the particle diameter.

In diffraction-based sizing techniques the particle interaction with the illumination is assumed to be analogous to the interaction of the same illumination with a uniformly illuminated circular aperture. The inherent problem in diffraction methods lies in the assumption that a particle acts as a uniformly illuminated aperture, which ignores many other scattering effects present in light scattering from a spherical particle, such as specular reflection, interference and refraction effects. Therefore, the Mie scattered signal has been used for determining particle characteristics.

The technique of Laser Sheet Dropsizing (LSD) has been used to determine droplet diameters. LSD uses the Mie signal, which is proportional to the particle diameter squared, and the Laser Induced Fluorescence (LIF) signal, which is proportional to the particle diameter cubed, for determining particle size.

Mie scattering has been investigated from small particles in the regime where the particle image is dominated by diffraction to determine the minimum particle diameter that is detectable for use in pulsed laser velocimetry techniques. Taking the Fourier transform of the Mie scattered electric fields from spherical particles results in multiple peaks in the intensity profile, the characteristics of which can be related to the particle size.

The ratio of the projected area of the reflection glare spot to the cross-sectional area of the droplet has been found to be proportional to the square of the ratio of the aperture radius to the distance from the droplet to the sensor surface. The signal to noise ratio of the light scattered from a spherical water droplet of known size is used as a measure of the ratio of light scattered from the glare spot to light scattered by the other part of the sphere surface. This information is then used to predict the shape and size of the reflection glare spot. Hence, information contained only in the reflection glare spot has been related to the droplet size. However, until now particle sizes (diameters) have not been determined as a function of the distance between a reflection glare spot and a transmission glare spot.

The present invention provides a new and improved apparatus and method which overcomes the above-referenced problems and others.

SUMMARY OF THE INVENTION

A method for determining a mass flux of an entrained phase in a planar two-phase flow records images of particles in the two-phase flow. Respective sizes of the particles are determined as a function of a separation between spots identified on the particle images. Respective velocities of the particles are determined. The mass flux of the entrained phase is determined as a function of the size and velocity of the particles.

In accordance with one aspect of the invention, the recording step includes recording an image of a transparent particle.

In accordance with another aspect of the invention, glare spots are identified on the particle. The particle size is determined as a function of a separation between the glare spots.

In accordance with another aspect of the invention, the step of determining the velocity includes determining the velocity as a function of a velocimetry of the particles within the images.

In accordance with a more limited aspect of the invention, the step of determining the velocity as a function of the velocimetry includes obtaining two exposures of the respective glare spots and measuring a displacement between the two exposures during a specified time interval. Either the average displacement (correlation processing) or individual particle displacements can be estimated depending on the data processing technique applied and the concentration of seed particles.

In accordance with another aspect of the invention, the step of determining the velocity as a function of the velocimetry includes detecting a Doppler shift of light.

One advantage of the present invention is that it makes in situ measurements without disturbing a flow field.

Another advantage of the present invention is that it provides a non-intrusive optical technique that offers instantaneous measurements of particle size and velocity at multiple spatial points in planar (2-D) fields, thereby permitting an estimate of mass flow to be obtained.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

A technique making use of the characteristics of the glare spots predicted by Mie theory is used in the present invention for particle sizing using Digital Particle Image Velocimetry (DPIV). A DPIV system is used to image the light scattered from spherical particles under controlled conditions at an observation angle of 90°. This recorded signal is representative of the Fourier transform of the Mie scattered electric fields incident on the lens of the imaging system. An evaluation of the present invention has been performed via a computer simulation program, which incorporates Mie theory and the Fourier transform properties of lenses on the scattered electric field. The location of the glare spots resulting from reflected and transmitted rays in the direction of observation are an indicator of particle size. While this measurement technique is not as accurate as point measurement techniques such as Phase Doppler Particle Analysis (PDPA), it has the potential for providing reasonable accuracy for size and high accuracy for velocity estimates in planar 2-D fields so that mass flow rates can be determined. The determination of mass flow rates are essential in many production type facilities (e.g., coal furnaces). Experiments have been performed to verify the simulation and to determine the feasibility of the present technique for measuring particle size from Digital Particle Image Velocimetry (DPIV) imagery.

Mie Theory Background

Mie theory provides the exact solution of electromagnetic waves scattered from a spherical particle that includes all of the diffraction, specular reflection, interference, and refraction effects. At an observation angle of 90°, two (2) glare spots are distinguishable on the surface of a transparent absorbing particle. The positions of these glare spots are described in Mie theory as a function of the particle diameter, the relative refractive index, and the angle from the optical axis at which the particle is being viewed. Knowledge of these positions is used to characterize the particles.

Figure 1:
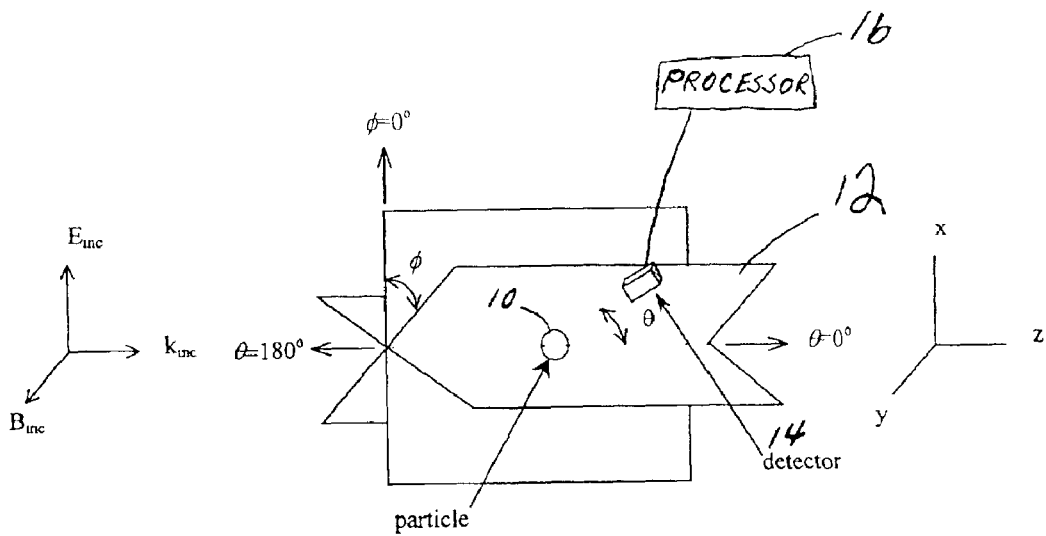
FIG. 1 illustrates scattering angles, θ and Φ, used in a Mie Scattering algorithm.

The Mie scattering problem defined here assumes plane wave illumination with the electric field $\vec{E}$ polarized in the x-direction (perpendicular to the scattering (y-z) plane) incident on a homogeneous, absorbing sphere in a non-absorbing medium. This polarization is referred to as s-polarization or transverse electric (TE) polarization. With reference to FIG. 1, a particle 10 within a two-phase flow is assumed to be in focus at the CCD detector plane. Angles θ and φ are defined from the x and z axes to a scattering plane 12 in which a detector (e.g., CCD camera) 14 is located. $E_{inc}$, $B_{inc}$, and $k_{inc}$ are the electric and magnetic fields and the propagation direction of the incident illumination. The detector 14 communicates with a processing device 16, which, as discussed below, calculates the size and velocity of the particle 10.

Figure 2:
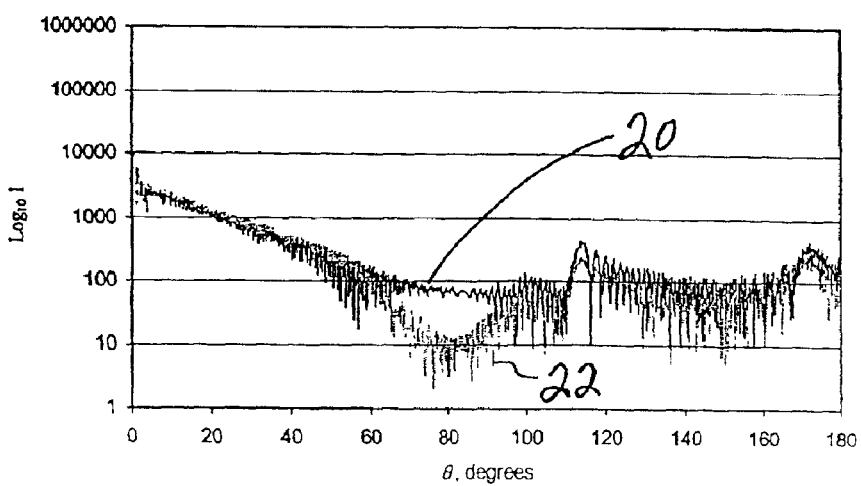
FIG. 2 illustrates a scattered intensity as a function of θ for a 100 μm diameter PSL sphere in water with 532 nm wavelength illumination.

The Mie scattering solution has been derived for the problem of the scattering of plane electromagnetic waves from a sphere. The magnitude of the scattered intensity is defined in Equation 1 as:

$$I_{scattered} = \frac{E_o^2}{2\mu_o c} \frac{1}{r^2 k^2} [|S_1(\theta)|^2 \sin^2\varphi + |S_2(\theta)|^2 \cos^2\varphi] \quad (1)$$

where $E_0$ is the magnitude of the incident electric field, $S_1$, and $S_2$ are the scattering amplitudes for the $\phi$ and $\theta$ polarizations of the scattered light, respectively, $\mu_0$ is the permeability of free space, c is the speed of light, r is the distance from the particle to the detector plane, and k is the propagation constant. This relation shows the polarization dependence of the scattered electric field from a particle at the observation angles $\theta$ and $\phi$. In the case of PIV imaging, the $\theta$ range is about 90° and the $\theta$ and $\phi$ range is about 0° or 90°, depending on whether the incident electric field is parallel (p-polarized, or transverse magnetic (TM) polarized incident light) or perpendicular (s-polarized or TE polarized incident light) to the scattering plane. When $\phi=0°$, the $S_1$ contribution is negligible since sin 0° is equal to zero (0). Conversely, when $\phi=90°$ the $S_2$ contribution is negligible. For s-polarized light ($\phi=90°$), the reflection and transmission glare spots are approximately equal in amplitude and this is the preferred illumination state. For p-polarized light ($\phi=0°$), the transmission glare spot is significantly dimmer than the reflection glare spot, which is not the preferred condition for obtaining accurate estimates of the glare spot peak locations. FIG. 2 shows how the $S_1$ and $S_2$ electric fields 20, 22, respectively, vary over a typical range of $\theta$ values.

When the incident light is unpolarized, or randomly polarized, the magnitude of the scattered intensity is defined in Equation 2 as:

$$I_{scattered} = \frac{E_o^2}{2\mu_o c} \frac{1}{r^2 k^2} \left[ \frac{1}{2}|S_1(\theta)|^2 + \frac{1}{2}|S_2(\theta)|^2 \right] \quad (2)$$

which has equal contributions of $S_1$, and $S_2$ scattered electric fields.

The light scattered by the particles is imaged onto a detector in order to make a measurement. The work done on the electric field imaged onto a CCD array by a lens is analogous to taking the Fourier transform of the input electric field. Taking the Fourier transform of the electric field signal and multiplying it by its complex conjugate yields the light intensity distribution on the CCD array (see Equation 3).

$$I_{scattered} = \Im(E^*_{scattered}) \cdot \Im(E_{scattered}) \quad (3)$$

where $\Im$ is the Fourier Transform, * represents the complex conjugate, $I_{scattered}$ is the scattered intensity imaged on the CCD detector and $E_{scattered}$ the scattered electric field at the lens plane of the optical system. This form of the signal makes the scattering effects, such as reflection and transmission, visible in the form of glare spot structures in the particle image.

Glare Spots

Figure 3:
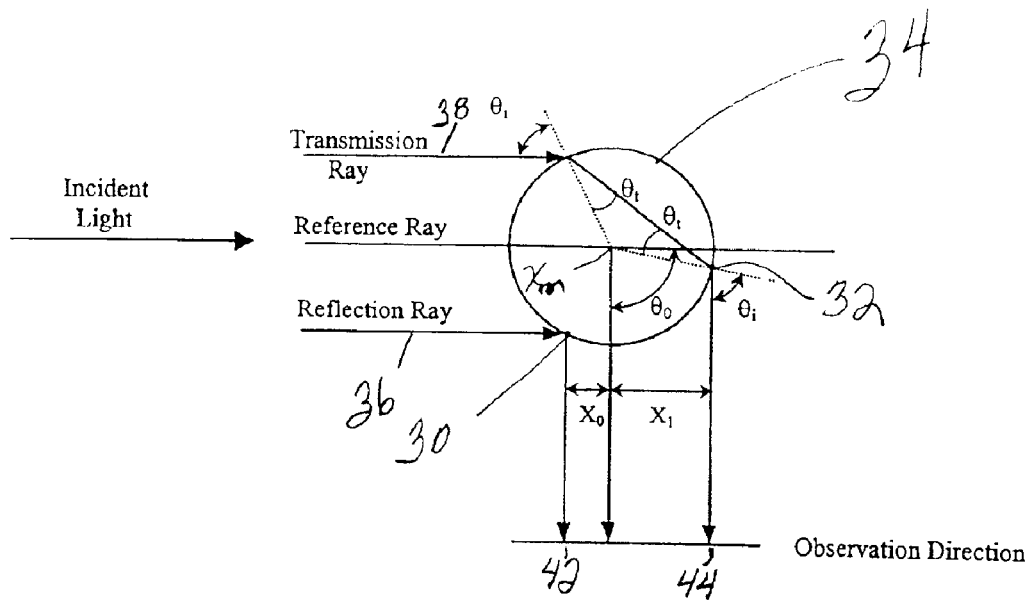
FIG. 3 illustrates the production of transmission and reflection glare spots.

With reference to FIG. 3, glare spots 30, 32 are bright spots resulting from off-axis light scattering by a spherical particle 34. According to ray theory a glare spot is seen at the exit points of any rays reflected or refracted in the direction of the observer. FIG. 3 demonstrates ray theory for the reflected rays 36 and transmitted rays 38 at a 90° observation angle. The points 42 and 44 correspond to the reflected and transmitted glare spots 30, 32, respectively. The ray denoted as the reflection ray 36 hits the surface of the spherical particle 34 and is reflected from the surface in the direction of observation. The ray denoted as the transmission ray 38 is internally reflected once and is then transmitted out of the particle 34 in the direction of observation.

The distance $X_0+X_1$ between the glare spots 30, 32 is directly related to the diameter of the particle 34. Therefore, it is possible to use the glare spot characteristics to determine particle/droplet sizes. As the particle diameter increases so does the separation distance between the glare spots. The glare spots 30, 32 are oriented in the direction of propagation of the incident light. The location of glare spots is calculated based on the size parameter (2 $\pi a/\lambda$), where a is the particle radius and $\lambda$ is the illumination wavelength), and the observation angle, $\theta_0$, by studying the Fourier transform of the geometric scattering amplitudes and the Mie scattered electric fields. The essence of the invention consists of estimating the particle size from a particle image on a CCD detector.

The glare spot positions relative to the particle centroid, $x_m$, in the object plane are determined and then related to the size parameter and observation angle. Therefore, if the positions are known at a specific observation angle, the size of the particle may be determined. The positions of the reflection and transmission glare spots on the detector plane are defined as:

$$x_o = -aM\cos\frac{\theta_o}{2} \quad (4)$$

$$x_1 = naM\sin\frac{\theta_o}{2}\left[n^2 + 1 - 2n\cos\frac{\theta_o}{2}\right]^{\frac{1}{2}} \quad (5)$$

where n is the ratio of the index of refraction of the particle material to the index of refraction of the medium, a is the particle radius, and M is the optical system magnification. The measured separation between the glare spots on the CCD detector leads to determination of the particle diameter $d_p$ via the following formula:

$$d_p = \frac{2\Delta\varepsilon_p}{\left|-M\cos\frac{\theta_o}{2}\right| + \left|\frac{nM\sin\frac{\theta_o}{2}}{\sqrt{n^2 + 1 - 2n\cos\frac{\theta_o}{2}}}\right|} \quad (6)$$

where $\Delta$ is the number of pixels separating the glare spots, $\epsilon_p$ is the CCD pixel size, M is the optical system magnification, n is the relative index of refraction, and $\theta_0$ is the observation angle. This relation is used to analyze data obtained from PIV images to estimate particle sizes in a flow field.

Using Glare Spot Separation to Estimate Particle Diameter

Figure 4:
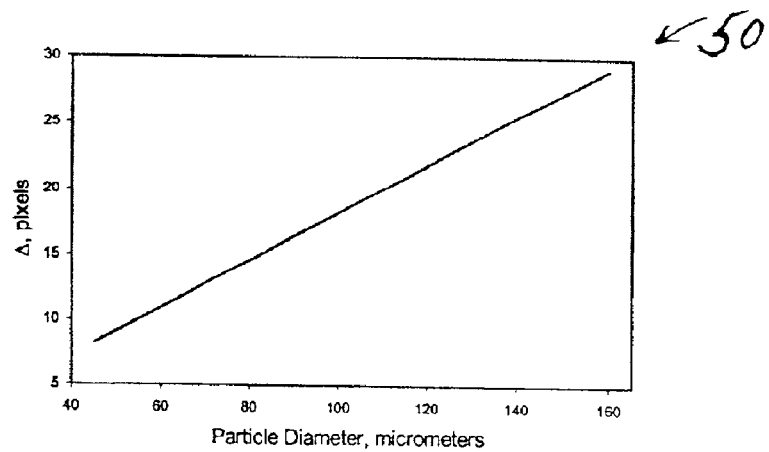
FIG. 4 illustrates glare spot separation as a function of particle diameter.

A one-to-one correspondence exists between the particle size and the glare spot separation according to Mie theory. Equation (6) gives the particle diameter in micrometers as a function of glare spot separation, $\Delta$, in pixels, CCD pixel size, $\epsilon_p$, in micrometers per pixel, relative index of refraction, n, optical system magnification, M, and observation angle, $\theta_0$. FIG. 4 shows a plot 50 of glare spot separation as a function of particle diameter based on this equation for a polystyrene latex sphere in water ranging in diameter from 45 $\mu$m to 160 $\mu$m with M=0.31, $\epsilon_p$=6.7 $\mu$m/pixel, n=1.195, and $\theta_0$=90°. The separation with respect to particle diameter is linear showing a one-to-one relationship between the glare spot separation and the particle diameter. Therefore, the glare spot separation is a viable indicator of the particle size. However, due to the low spatial resolution of a CCD camera, it is still difficult to extract the particle sizes to high accuracy based on the spot separation.

The accuracy of the particle size estimates is determined by the accuracy by which the two (2) glare spot peaks are determined. It has been shown that the uncertainty in estimating the center location of a Gaussian signal is proportional to the ratio of the width of the signal to the square root of its amplitude. In standard PIV data processing, the particle images or correlation peaks are typically estimated within an accuracy of about 0.2 pixels, provided the particle images span 1–2 pixels across their width. The glare spots from the particle images satisfied this criterion. Hence, the glare spot separation is estimated to an accuracy of about $\sqrt{2}$ (0.2), providing particle size estimates with accuracies on the order of $\sqrt{2}$ (0.2)/$\Delta$. The error in estimating particle size is inversely proportional to the number of pixels separating the glare spots. Therefore, the CCD camera used for such measurements must have sufficient resolution (high pixel count) to distinctly image the glare spots.

Description of Planar Size and Velocity Measurement Technique

A technique making use of the characteristics of the glare spots predicted by Mie theory is used in the present application of simultaneous measurement of particle size and velocity using PIV. A PIV system is used to image the light scattered from spherical particles at an observation angle of 90°. This recorded signal is representative of the Fourier transform of the Mie scattered electric fields incident on the lens of the imaging system. As shown in the previous section, the location of the glare spots resulting from reflected and transmitted rays in the direction of observation is a good indicator of particle size. Recall that it is crucial to have sufficient spatial resolution to image the glare spots. This becomes very important with small particles where the glare spot separation is minimal. The centroids of the glare spot peaks, and hence the separation between the glare spots, are determined using a three-point Gaussian peak estimate technique. Using Equation (6), the particle diameter is calculated based on the measured glare spot separation and the optical system parameters. Software for performing the size estimations is described in the next section. Velocity estimates are obtained via PIV correlation processing performed on the same images using any commercial or custom PIV processing software. Once the size and velocity are obtained, the mass flux of the particle is determined according to conventional techniques. Alternatively, particle tracking velocimetry techniques can be employed, wherein the individual particle velocities are determined, which can be directly matched to the individual particle size estimates obtained from the glare spot separation.

Sizing

Figure 5:
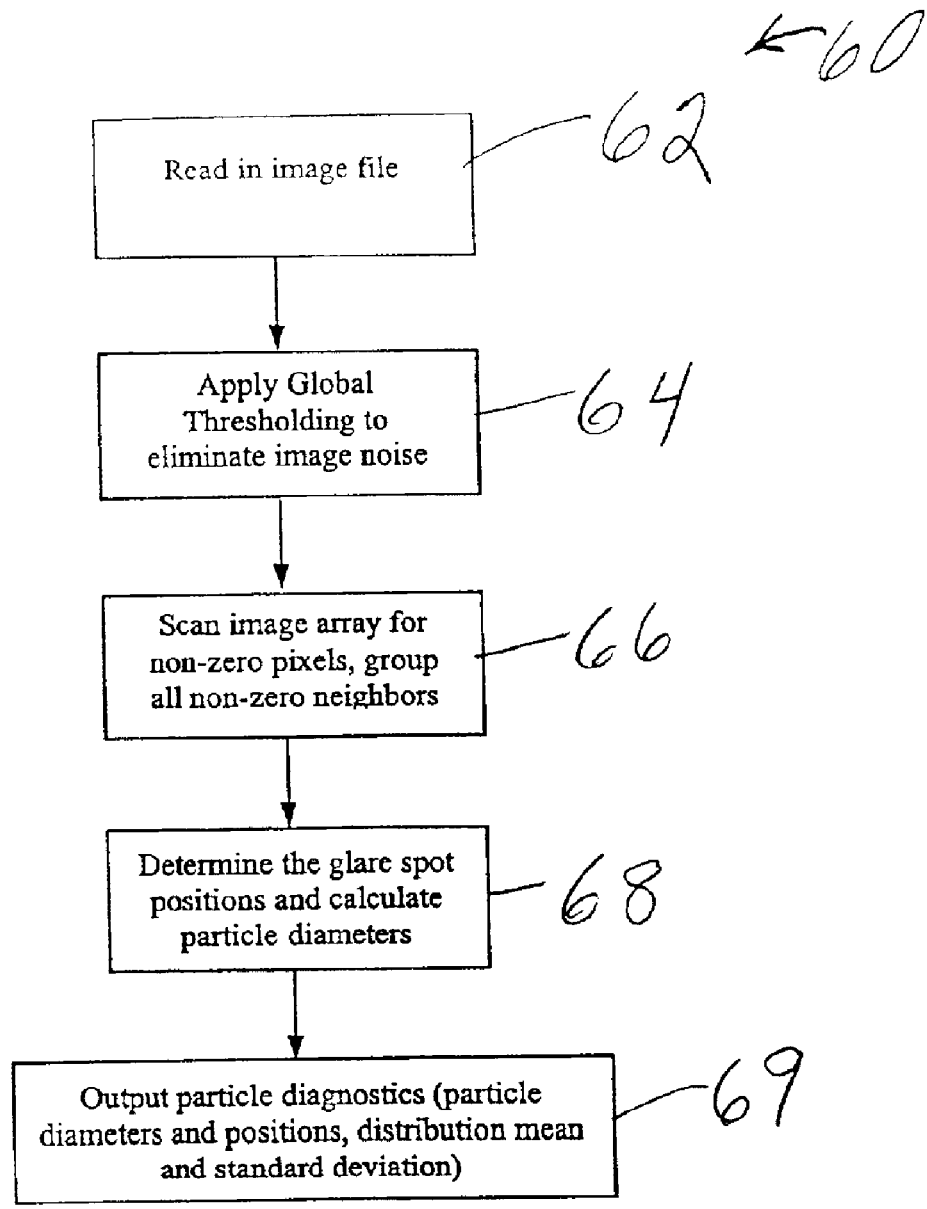
FIG. 5 illustrates an algorithm for scanning PIV images and determining the size of detected particles.

With reference to FIG. 5, an algorithm 60 has been developed to scan the PIV images for particle images and determine the size of each particle detected. An image file is read in a step 62. Thresholding is applied within the image (e.g., global thresholding), in a step 64, to reduce noise within the image. Global thresholding imposes a user-defined value that limits the minimum non-zero intensity value of the image. Any pixels below the threshold value are set to zero (0). The thresholding eliminates background noise in the image, thereby making it easier to discriminate particle images from the background and aiding in the separation of overlapping particles. It is important not to pick a threshold level so high that the two (2) glare spots are separated from each other. Alternatively, a local adaptive thresholding technique could also be employed. Local thresholding would offer better image extraction than a global technique, since variations in background levels in the image typically require a higher than optimum global threshold level setting.

The image pixel array is scanned in a step 66. Preferably, the image is scanned from left to right, and top to bottom for non-zero (0) pixels. Whenever a non-zero pixel is found, the eight (8) adjacent pixels are scanned and any non-zero pixels are grouped along with the initial pixel to form a particle image array. Then the eight (8) adjacent pixels to each of the non-zero pixels are scanned and non-zero pixels are grouped into the same particle image array. Pixels cannot belong to more than one (1) of the particle image arrays.

Scanning continues until no more adjacent non-zero pixels are found and the next particle image is found. Each particle image array is analyzed to determine if the image is saturated (i.e., more than one (1) pixel in the array has the maximum intensity value as determined by the dynamic range of the camera). The sizing algorithm does not accommodate saturated images since it is difficult to accurately determine the locations of the glare spots within the particle image when they are saturated. Therefore, saturated particle images are rejected.

The glare spot positions and particle diameter are determined in a step 68. If the particle is not saturated, the maximum intensity in the image is found. The values of the pixels above and below, and to the right and left of the maximum intensity pixel are used to calculate the 3-point Gaussian estimate of the glare spot centroid. Next, the particle image array is scanned to the left and right (or top and bottom in the case of a vertical propagating light sheet) to find the point where the slope of the intensity distribution curve changes sign, indicating the start of the second glare spot. The particle image array is then scanned from the point of slope change to the edge of the array, continuing in the same scanning direction, in search of the maximum intensity within that area of the array. This maximum intensity indicates the location of the second glare spot. The same 3-point Gaussian estimate approach is taken to estimate the second glare spot centroid. The difference between the centroid positions represents the variable $\Delta$ in Equation 6 for calculating the particle image diameter. This same process is followed for every particle image array within the entire PIV image.

If no slope change is found, then a second glare spot does not exist and that particle is rejected. The particle may be too small to distinguish between the two (2) separate glare spots and, therefore, sizing is not possible using this method. The locations of the sized particle images and the calculated diameter are output to a file.

Particle diagnostics (e.g., diameter, position, distribution mean, and standard deviation) are output to a processor in a step 69.

Figure 6:
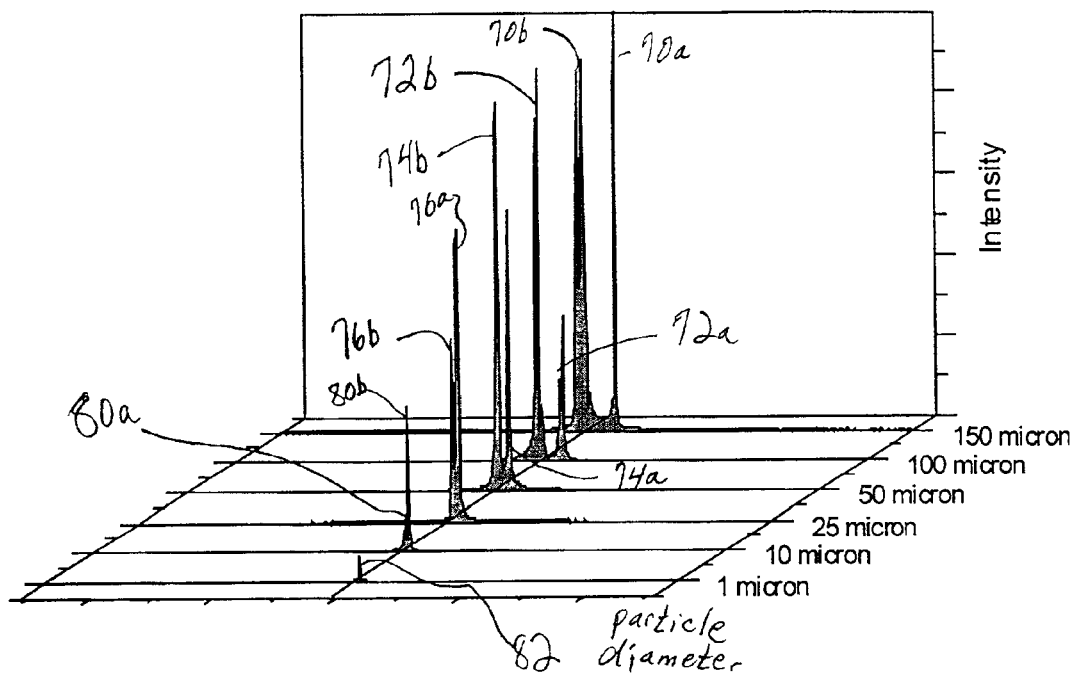
FIG. 6 illustrates glare spot intensity fields for a range of particle diameters.

FIG. 6 illustrates glare spot intensity fields for a range of particle diameters. Note that intensity fields 70a, 70b, 72a, 72b, 74a, 74b, 76a, 76b, 80a, 80b, 82 are very well defined for particles having relatively larger diameters. For example, the glare spot intensity fields 70a, 70b for a particle having a diameter of 150 microns are much more defined than the intensity fields 80a, 80b for a particle having a diameter of 1 micron. The intensity field 82 only indicates a single glare spot and, therefore, would be rejected by the algorithm described above.

The preferred embodiment of the present invention has been described with respect to estimating the particle size as a function of glare spot separations. However, it is also contemplated to determine particle sizes as a function of a ratio of the amplitude of the glare spot intensities.

Furthermore, it is also contemplated to estimate the diameter of the particle by iteratively computing the electric field scattered by a particle and determining the resultant electric field detected by the CCD sensor. The process is repeated until the correct particle size is determined. Convergence to the correct particle size is determined when the computed image of the electric field on the CCD sensor matches the measured glare spot separation and intensity distribution for a given particle image.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method for determining a mass flux of a particle, comprising:

recording an image of the particle entrained in a two-phase flow, using a camera; and using a processor for determining a size of the particle as a function of a separation between spots identified on the particle, determining a velocity of the particle, and determining the mass flux of the particle as a function of the size and velocity, wherein the spots are glare spots and the separation between the glare spots is determined as:

$$x_o = -aM\cos\frac{\theta_o}{2};$$

$$x_1 = naM\sin\frac{\theta_o}{2}\left[n^2 + 1 - 2n\cos\frac{\theta_o}{2}\right]^{\frac{1}{2}}; \text{ and}$$

$$d_p = \frac{2\Delta\epsilon_p}{\left|-M\cos\frac{\theta_0}{2}\right| + \left|\frac{nM\sin\frac{\theta_0}{2}}{\sqrt{n^2 + 1 - 2n\cos\frac{\theta_0}{2}}}\right|},$$

where $d_p$ is an estimate of the particle diameter, n is a ratio of an index of refraction of a material of the particle to an index of refraction of a medium, a is a radius of the particle, M is an optical system magnification, $\Delta$ is a number of pixels separating the glare spots on a surface of a CCD, $\epsilon_p$ is a size of the pixels in the CCD, and $\theta_o$ is an observation angle.

2. The method for determining a mass flux of a particle as set forth in claim 1, wherein the recording step includes:

recording an image of a transparent particle.

3. The method for determining a mass flux of a particle as set forth in claim 1, further including:

identifying glare spots on the particle, the particle size being determined as a function of a separation between the glare spots.

4. The method for determining a mass flux of a particle as set forth in claim 1, wherein the step of determining the velocity includes:

determining the velocity as a function of a velocimetry of the particles within the images.

5. The method for determining a mass flux of a particle as set forth in claim 4, wherein the step of determining the velocity as a function of the velocimetry includes:

obtaining two exposures of the respective glare spots of the particles entrained in the fluid; and measuring a displacement between the two exposures during a specified time interval.

6. The method for determining a mass flux of a particle as set forth in claim 4, wherein the step of determining the velocity as a function of the velocimetry includes:

detecting a Doppler shift of light.

7. An optical flow meter for determining a mass flux of a particle, comprising:

a camera for recording an image of the particle entrained in a two-phase flow; and a processor for determining a size of the particle as a function of a separation between spots identified on the particle, determining a velocity of the particle, and determining the mass flux of the particle as a function of the size and velocity, wherein the spots are glare spots and the separation between the glare spots is determined as:

$$x_o = -aM\cos\frac{\theta_o}{2};$$

$$x_1 = naM\sin\frac{\theta_o}{2}\left[n^2 + 1 - 2n\cos\frac{\theta_o}{2}\right]^{\frac{1}{2}}; \text{ and}$$

$$d_p = \frac{2\Delta\epsilon_p}{\left|-M\cos\frac{\theta_0}{2}\right| + \left|\frac{nM\sin\frac{\theta_0}{2}}{\sqrt{n^2 + 1 - 2n\cos\frac{\theta_0}{2}}}\right|},$$

where $d_p$ is an estimate of the particle diameter, n is a ratio of an index of refraction of a material of the particle to an index of refraction of a medium, a is a radius of the particle, M is an optical system magnification, $\Delta$ is a number of pixels separating the glare spots on a surface of a CCD, $\epsilon_p$ is a size of the pixels in the CCD, and $\theta_o$ is an observation angle.

8. The optical flow meter for determining a mass flux of a particle as set forth in claim 7, wherein a Gaussian peak location estimate is used for determining a location of respective peaks of the glare spots, the separation between the glare spots being determined as a function of the locations of the peaks.

9. The optical flow meter for determining a mass flux of a particle as set forth in claim 7, wherein the camera is a CCD camera.

10. The optical flow meter for determining a mass flux of a particle as set forth in claim 7, wherein the particles are transparent.

11. A method for determining a size of a particle, the method comprising:

receiving an image of the particle entrained in a two-phase flow into a processor;

reducing background noise within the image;

grouping the pixels having non-zero values into respective particle image arrays;

identifying glare spots within the image as a function of the particle image arrays; and determining the size of the particle as a function of a separation between the glare spots, wherein the separation between the glare spots is determined as:

$$x_o = -aM\cos\frac{\theta_o}{2};$$

-continued $$x_1 = naM\sin\frac{\theta_o}{2}\left[n^2 + 1 - 2n\cos\frac{\theta_o}{2}\right]^{\frac{1}{2}}; \text{ and}$$

$$d_p = \frac{2\Delta\varepsilon_p}{\left|-M\cos\frac{\theta_0}{2}\right| + \left|\frac{nM\sin\frac{\theta_0}{2}}{\sqrt{n^2 + 1 - 2n\cos\frac{\theta_0}{2}}}\right|},$$

where $d_p$ is an estimate of the particle diameter, n is a ratio of an index of refraction of a material of the particle to an index of refraction of a medium, a is a radius of the particle, M is an optical system magnification, $\Delta$ is a number of pixels separating the glare spots on a surface of a CCD, $\epsilon_p$ is a size of the pixels in the CCD, and $\theta_o$ is an observation angle.

12. The method for determining a size and a velocity of a particle as set forth in claim 11, wherein the reducing step includes:

limiting non-zero intensity values of pixels within the image.

13. The method for determining a size and a velocity of a particle as set forth in claim 12, wherein the limiting step includes:

determining a global threshold intensity value for the pixels within the image; and setting intensity values of pixels below the global threshold to zero.

14. The method for determining a size and a velocity of a particle as set forth in claim 13, further including:

determining a local threshold for discriminating the particle within the image.

15. The method for determining a size and a velocity of a particle as set forth in claim 11, wherein the grouping step includes:

scanning the image for the pixels having the non-zero values;

identifying one of the pixels as having the non-zero value;

identifying pixels adjacent to the pixel having the non-zero value;

grouping any of the adjacent pixels having the non-zero values into the particle image array;

identifying subsequent pixels adjacent to each of the adjacent pixels having the non-zero value; and grouping any of the subsequent pixels into the particle image array.

16. The method for determining a size and a velocity of a particle as set forth in claim 11, further including:

rejecting ones of the particle image arrays that are saturated.

* * * * *